United States Patent [19]

Howe et al.

[11] Patent Number: 4,710,259

[45] Date of Patent: Dec. 1, 1987

[54] SETTING THE ORIENTATION OF CRYSTALS

[76] Inventors: Stephen H. Howe, 4 Scariff Court, 39 Sycamore Grove, New Malden, Surrey; Donald Rogers, 11 Salvington Crescent, Bexhill-on-Sea, East Sussex, both of United Kingdom

[21] Appl. No.: 740,043

[22] PCT Filed: Sep. 24, 1984

[86] PCT No.: PCT/GB84/00324

§ 371 Date: May 14, 1985

§ 102(e) Date: May 14, 1985

[87] PCT Pub. No.: WO85/01349

PCT Pub. Date: Mar. 28, 1985

[51] Int. Cl.⁴ .................. C30B 33/00; C30B 15/20
[52] U.S. Cl. ................... 156/601; 156/617 SP; 156/DIG. 65; 378/73
[58] Field of Search ............ 378/73, 83; 156/601, 156/617 SP, DIG. 65

[56] References Cited

U.S. PATENT DOCUMENTS 3,213,278 10/1965 Spielberg ........................ 378/49
3,345,613 10/1967 Bucholtz et al. ............... 340/172.5
3,788,890 1/1974 Mader et al. .................... 156/601
3,870,880 3/1975 Merigoux et al. ............... 378/73

FOREIGN PATENT DOCUMENTS 174598 10/1984 Japan ........................... 156/601

Primary Examiner—Gary P. Straub
Attorney, Agent, or Firm—Kane, Dalsimer, Sullivan, Kurucz, Levy, Eisele and Richard

[57] ABSTRACT

A method of and apparatus for setting the orientation of a single crystal which may be a seed crystal, boule, wafer or a growing boule. The crystal is irradiated with a beam of X-rays having a peak of energy at a given wavelength and the orientation of the crystal is adjusted while moving the crystal and the beam about an axis perpendicular to the equatorial plane containing the X-ray beam until a pair of reflexions that are symmetrical with respect to the equatorial plane occur simultaneously at the said wavelength of radiation. When the X-ray beam has a peak of energy at the said wavelength against a back ground of white radiation, symmetrical reflexions can be detected and will flash simultaneously only when one of the crystallographic planes of symmetry is set in a predetermined or determinable orientation relative to a given datum. In contrast to conventional techniques which involve quantitative analysis or measurements of one diffracted beam at a time, the present invention depends only upon detecting simultaneous flashing of symmetrical reflexions above and below the equatorial plane, in order to set the orientation of a crystal with a high degree of accuracy.

7 Claims, 27 Drawing Figures

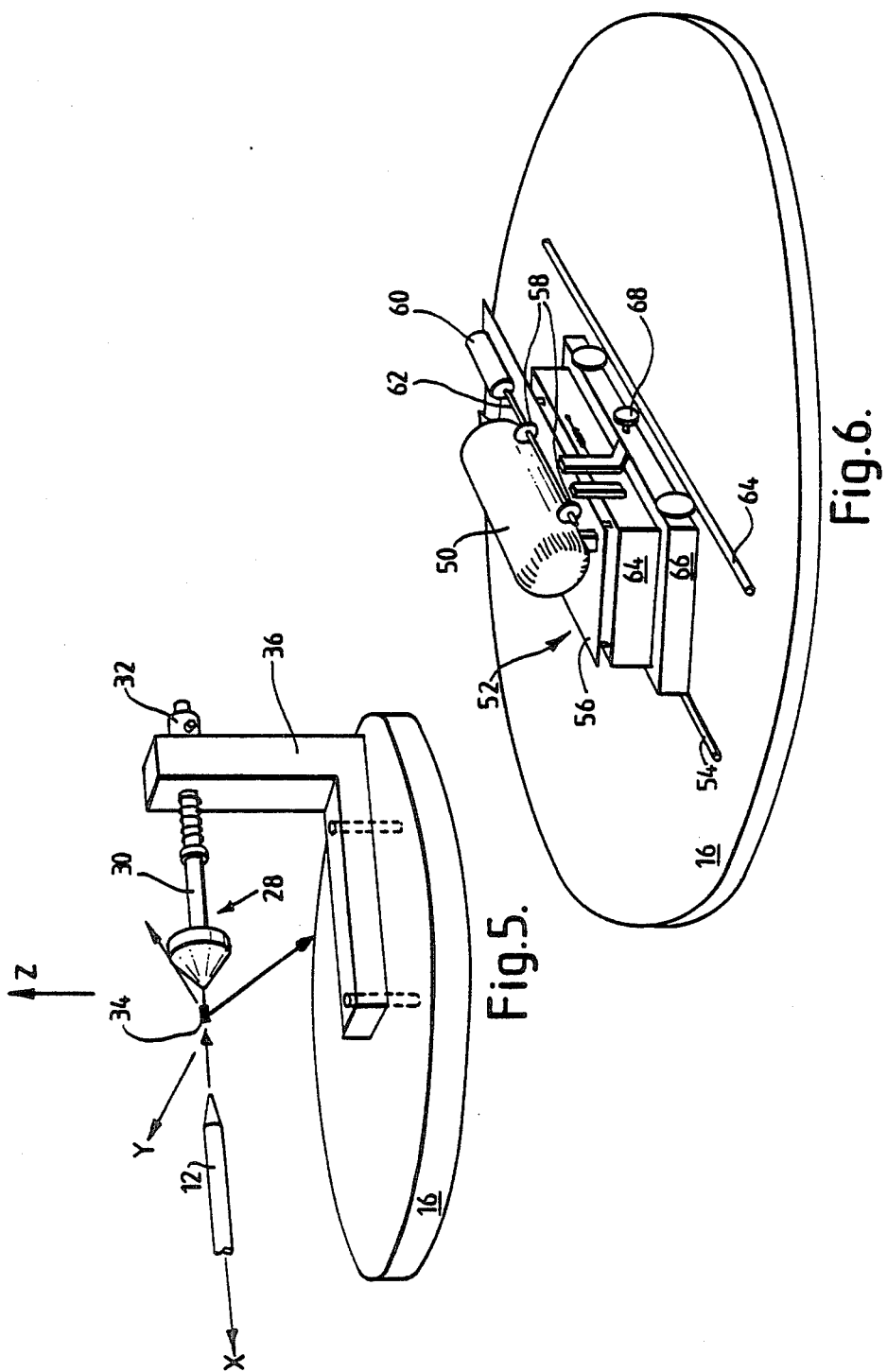

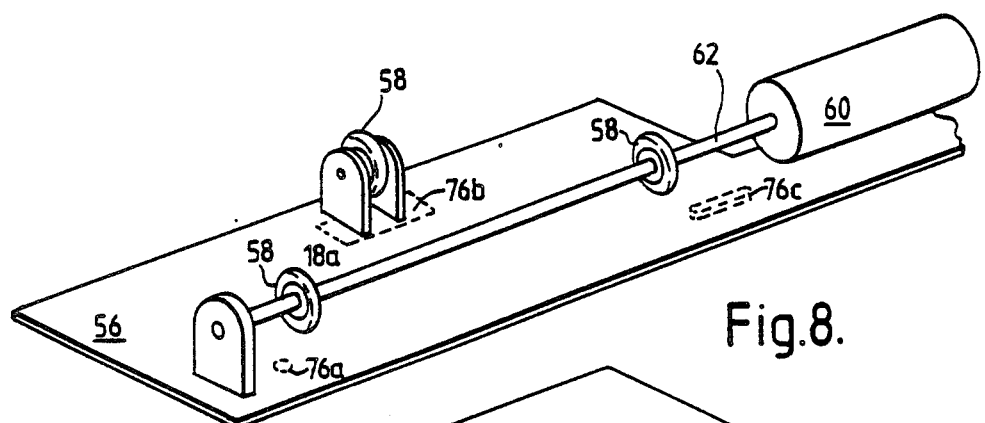
Fig.8.
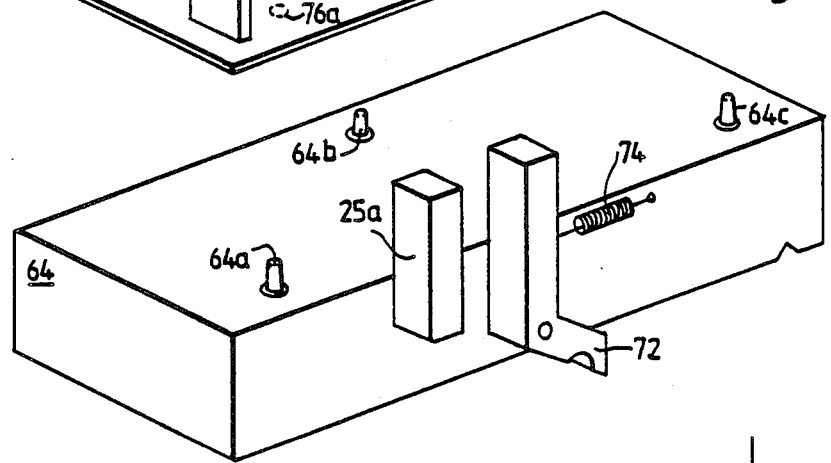
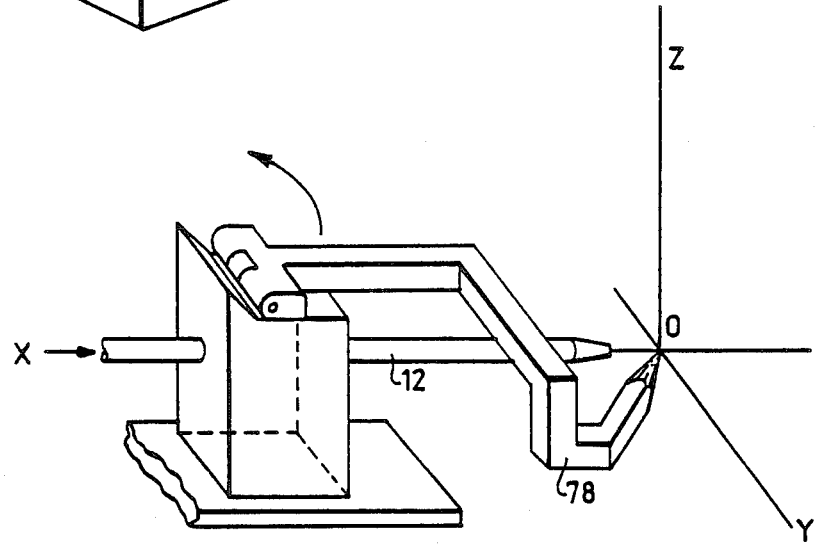
Fig.9.

SETTING THE ORIENTATION OF CRYSTALS

This invention relates to a method and apparatus for setting the orientation of the crystallographic axes of a single-crystal such as may be required preparatory to cutting a boule or polishing a wafer. It is applicable in both laboratory and industrial contexts and is especially relevant to the production of microchips from boules.

Current practice is to affix the boule to a base plate with epoxy-resin as a means of holding it while cutting, to determine the errors in the orientation of its crystallographic axes by means of an X-ray diffraction technique, and, having transferred the specimen on its base plate to the cutter/polisher, to make angular correctons on that instrument to ensure that the resulting surface has the desired orientation. Such methods usually employ monochromatic (characteristic) radiations and involve measurement of the Bragg angle of one diffracted beam at a time. Where comparison of two such beams is made they are profiled separately and, when accuracy is needed, this is a relatively slow process that calls for a stabilized X-ray source which is expensive. It also necessitates duplication of the angular correction facilities on the cutter/polisher.

The rate of deposition of epitaxial layers (or the depth of penetration of ion implantation) during the subsequent formation of integrated circuits on the surface of a wafer is markedly dependent on the degree of misalignment between the growth face and the crystallographic planes in the substrate, and the electronic switching speeds achievable in the finished product depend on the thickness of such deposits. It has become important, therefore, especially in the batch production of microprocessors, to control the orientation of the prepared surface of the wafers, and to make any deliberate misalignments that are desirable in the interests of high switching speeds as reproducible as possible: and that requires precise angular measurements. Sufficient accuracy is achievable with some of the current techniques but always at a high price in time.

One object of the invention is to enable high-precision setting to be achieved routinely, much more rapidly, and in a preferred embodiment, in a manner that lends itself to adjustment under computer control.

We have found that the orientation of a crystal can be determined with reference to a position in which a pair of symmetrical reflexions simultaneously satisfy Bragg's law at the same wavelength of X-ray radiation and propose therefore, in accordance with the invention to ascertain the orientation of a crystal by irradiating the crystal with an X-ray beam and detecting a pair of symmetrical reflexions which occurs at the same wavelength of X-ray radiation.

According to this invention a method of setting the orientation of a single crystal comprises directing onto the crystal an X-ray beam comprising a peak of energy at a given wavelength, adjusting the orientation of the crystal while relatively moving the crystal and the beam about an axis perpendicular to an equatorial plane containing the X-ray beam until any pair of relexions that are symmetrical with respect to the equatorial plane occur simultaneously (ie. at the same azimuth) at the said wavelength of X-ray radiation.

It will be understood that some or all of the energy in the X-ray beam must be confined to a very narrow bandwidth, in which case the pair of reflexions will occur simultaneously only when one of the crystallographic planes of symmetry is set in a predetermined or determinable orientation relative to a datum.

Most X-ray diffraction tubes will, in addition to white radiation, generate intense peak energy at a wavelength or wavelengths characteristic of the target material in the tube when operated above a critical voltage, so that in a preferred embodiment using a conventional X-ray diffraction tube it is possible to detect a pair of reflexions before making adjustments to establish a relative position of the beam and crystal in which the pair of relexions "flash" simultaneously in response to the peak energy, at the wavelength of the characteristic radiation. Hence, in contrast to conventional techniques requiring quantitative analysis or measurements to determine the crystal orientation, the present invention requires only the detection of simultaneous events.

In a preferred embodiment of this invention therefore, a method of orienting a single crystal comprises:

directing onto the crystal an X-ray beam that contains white radiation and an intense peak of energy at a given wavelength, detecting a pair of symmetrical reflexions, preferably steeply inclined to an equaterial plane containing the X-ray beam, at an angle in the range 30°–70°, relatively moving the crystal and the beam about an axis perpendicular to the equatorial plane, to detect when each of the reflexions flash, and adjusting the orientation of the crystal while relatively moving the crystal and the beam about the said perpendicular axis through the two flashing positions until the reflexions flash simultaneously. In this position the normals to the two sets of lattice planes are symmetrical to the plane normal to the said perpendicular axis (the equatorial plane).

For convenience, relative movement of the crystal and the beam about the the said perpendicular axis is a rocking movement between the two flashing positions, adjustments being made as necessary until the relexions flash or occur simultaneously.

When the crystal is a growing boule, however, such rocking movement is not practicable since the boule is required to rotate continously relative to the melt. In this case, the axis of rotation of the boule is arranged perpendicular to the equatorial plane and pairs of symmetrical reflexions are detected continously or at intervals as the boule is pulled from the melt, and adjustments are made as necessary until the reflexions in each pair flash or occur simultaneously.

It will be understood from the principles of X-ray diffraction, that a disturbance of a perfectly set crystal about an axis perpendicular to the X-ray beam destroys simultaneity whereas an equal disturbance about an axis parallel to the beam has no effect. Hence, it follows that the most effective adjustments in the method of this invention are those about an axis lying in or parallel to the equatorial plane and normal or nearly normal to the X-ray beam.

Also, the most useful relexions are those that flash at an azimuth normal or nearly normal to the X-ray beam. For this reason, it is preferred to locate the detection means with its axis at or near normal to the X-ray beam.

When setting a crystal, therefore, reflexions that flash as near as possible to the normal are selected. Adjustments are then made about an axis lying in or parallel to the equatorial plane and normal to the X-ray beam before turning the crystal through 90° about the said perpendicular axis and repeating the process with a second pair of reflexions.

Unless the selected reflexions are in fact normal to the beam, which is highly unlikely, the second adjustment will disturb the first but by a smaller error than the original misetting, so that the two steps are repeated alternately to convergence at the position in which the reflexions in each (or indeed any pair) flash simultaneously.

The invention is applicable not only to crystals and their orientations for which the pairs of Laue reflexions are symmetrical in both position and intensity but, more generally, to all crystals and their orientations that offer positional symmetry only, regardless of intensity. This less-limiting prerequisite makes the invention applicable to virtually all crystals presently or likely to be of practical significance for industrial or research purposes.

Also in accordance with the present invention we propose apparatus for setting the orientation of a single crystal, comprising an X-ray diffractometer including a source of a beam of X-rays, a crystal holder for supporting a crystal in the equatorial plane of the diffractometer containing the X-ray beam, such that the X-ray beam impinges thereon, adjusting means for effecting relative movement of the crystal and the beam about two perpendicular axes parallel to or lying in the equatorial plane, detecting means arranged and/or adapted to receive a pair of reflexions from the crystal steeply inclined to the equatorial plane both above and below the said plane, and means for effecting relative movement of the crystal and the beam back and forth about an axis perpendicular to the equaterial plane.

In contrast to conventional X-ray diffractometers, the apparatus of the present invention includes detection means capable of detecting reflexions from the crystals that are symmetrical above and below the equatorial plane and, further, steeply inclined thereto, preferably in the said range.

The detection means may comprise a single wide aperture detector, the solid angle subtended by the aperture of the detector preferably being in the range 1.5 to 3 steradions.

In a preferred embodiment, however, the detection means comprises two separate detectors such as scintillation counters, adjustably mounted respectively to receive the individual reflexions above and below the equatorial plane and steeply inclined thereto.

To permit automatic setting of the orientation of the crystal, the apparatus comprises control means responsive to changes in the output of the detectors during relative movement of the crystal back and forth about the said perpendicular axis, which movement may also be under control of the control means, and operable to activate the adjusting means in the sense toward a position wherein the pair of reflexions flash simultaneously.

Different crystal holders are required depending upon whether the crystal is a small specimen or seed crystal, a boule or a wafer. A turntable is provided to support the crystal holder and to enable angular displacement about the said perpendicular axis, the crystal holder affording four degrees of freedom for adjustment of the crystal position relative to the turntable both laterally in the equatorial plane and angularly about two perpendicular axes lying in or parallel to the equatorial plane. The crystal holder and/or the turntable also are adjustable in the direction of the said perpendicular axis, to set the crystal in the equatorial plane.

For adjusting and setting the orientation of a small specimen or seed crystal the crystal holder may be a standard goniometer such as will be well known to those skilled in the art. One form of crystal holder suitable for other purposes preferably comprises a platform which is freely supported by a jacking module having three jacks the heads of which engage recesses forming a hole/slot/plane locating system in the underside of the platform. This enables reproducible transfer of the platform, and with it the boule, from the diffractometer used to orientate the boule, to a wafer cutting device.

Lateral displacement of the platform, to move the crystal in the equatorial plane for example, to set the crystal such that the point of impingement of the X-ray beam coincides with the said perpendicular axis, is achieved by mounting the jacking module upon a bogie to form a carriage assembly to run along rails fitted to the turntable, and in a direction perpendicular to the rails, by slidably supporting the jacking module on the bogie for displacement transversely thereof.

A crystal holder of this kind can be used to ascertain as closely as possible the orientation of an unmounted boule which can then be affixed to a platform of the carriage assembly using an epoxy resin or other adhesive.

Accurate orientation of the boule is then achieved in two stages. The boule is mounted on the carriage assembly on the diffractometer and the turntable set such that the rails are initially approximately perpendicular to the X-ray beam, the boule is then advanced along the rails on the turntable in the direction of its longitudinal axis until the X-ray beam impinges upon its rounded end. Next, the turntable is rotated a little on either side of the set position until a symectrical pair of reflexions is detected. Once the flashing position is identified, small amplitude rocking is commenced about that position while at the same time adjusting the boule little by little about on axis in or parallel to the equatorial plane approximately normal to the X-ray beam, until a position is reached at which the pair of reflexions flash simultaneously.

The turntable is then displaced through approximately 90° to the end-on position. A new pair of flashing reflexions is found. Adjustment of the boule is then made about the same axis as before, to a position in which the reflexions flash simultaneously. In this second stage therefore, the adjustment can be made about the major axis of the boule. The boule is then moved in the direction of its longitudinal axis (along the rails) to check for uniformity of orientation along its length. A note can be made of any discontinuities and further checks carried out if necessary to identify the orientation of axes in the trimmed section. In this manner a precise cutting plan, wafer by wafer, can be prepared and if the crystal holder adjustments are performed remotely (eg. by a digital motor drive) under computer control, the cutting plan can be utilised for automatic control of the wafer cutting device.

After cutting, each wafer in turn can be transferred to, for example, a gimballed support plate, for orientation by the same technique and polishing in preparation for the application of thin layers of other materials by epitaxial growth or ion-beam implantation.

Embodiments of this invention will now be described by way of example with reference to the accompanying drawings in which:

FIG. 5 is a perspective view of the turntable to the apparatus shown in FIG. 3 but with the goniometer mounted horizontally;

FIG. 6 is a perspective view of the turntable of the apparatus for FIG. 3 but having thereon a carriage assembly for use in setting the orientation of an unmounted boule;

FIG. 8 is an exploded view of the carriage shown in FIG. 6;

FIG. 9 is a perspective view of a distance gauge for use in the apparatus of FIG. 6;

Figure 19A:
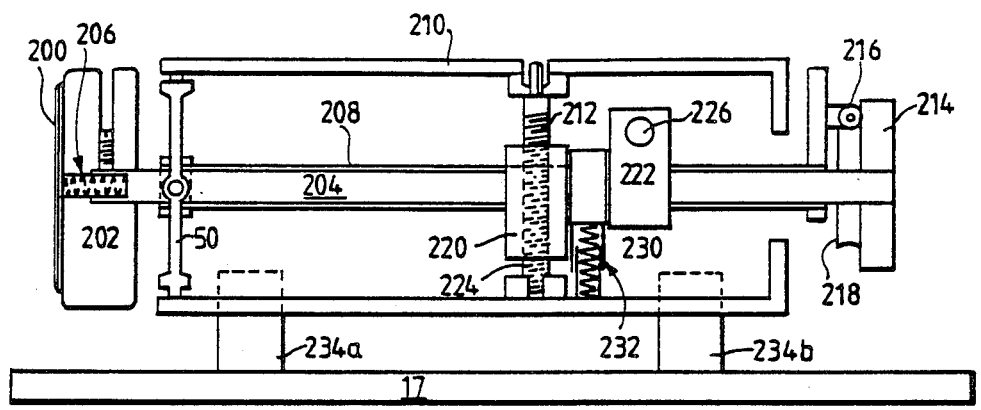
Figure 19B:
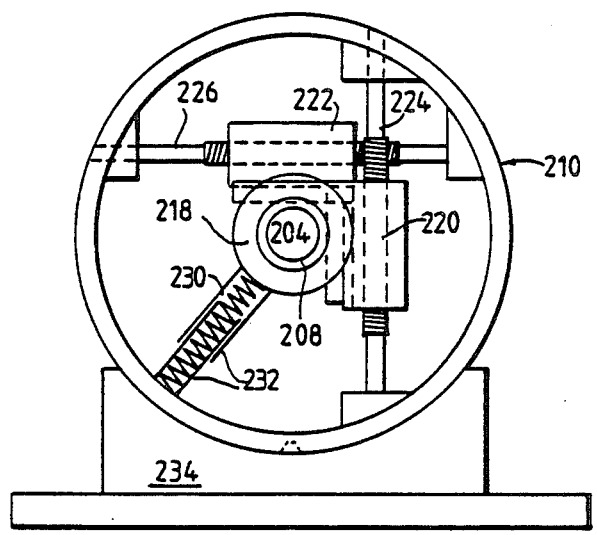
Figure 20A:
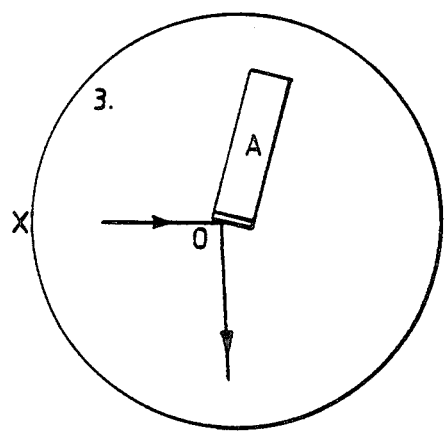
Figure 20B:
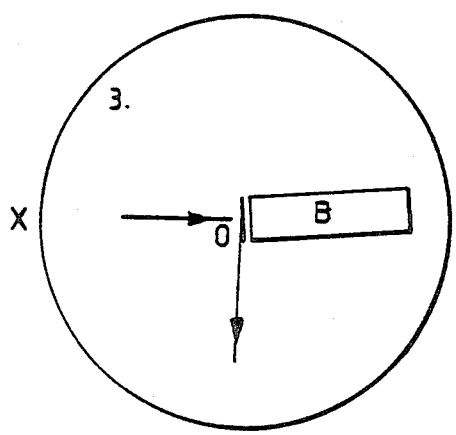
Figure 21:
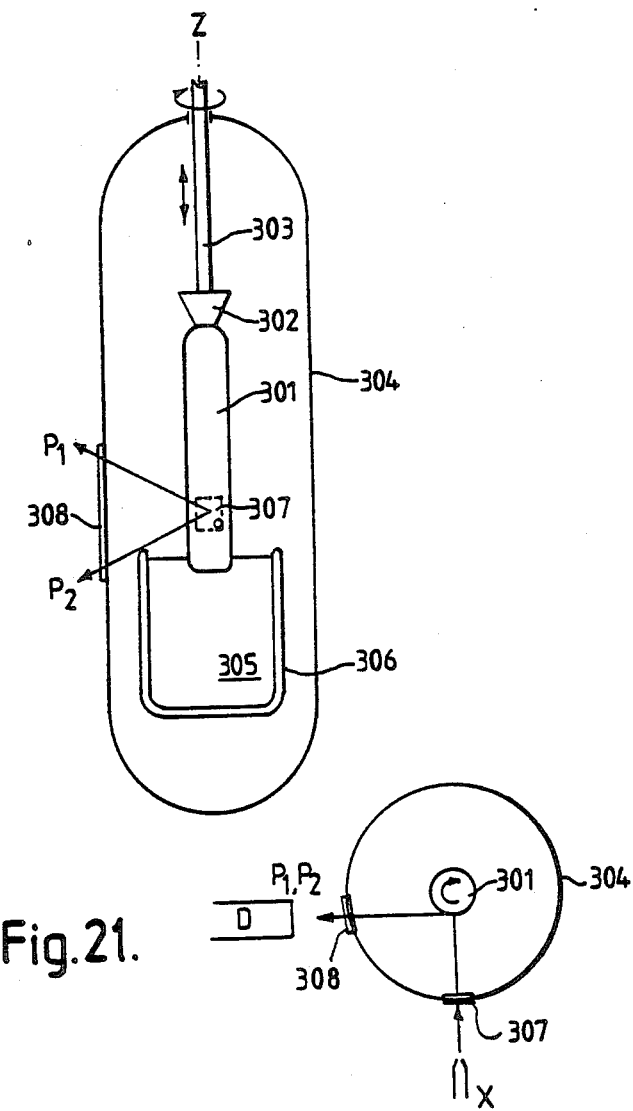

FIGS. 19a and 19b respectively are longitudinal and transverse cross-sections of a holder for a crystal wafer;

FIGS. 20a and 20b are diagrams illustrating different stages in setting the orientation of a wafer using a diffractometer fitted with a crystal holder such as shown in FIGS. 19a and 19b; and FIG. 21 schematically illustrates apparatus for setting and monitoring the orientation of a growing crystal boule.

Figure 1:
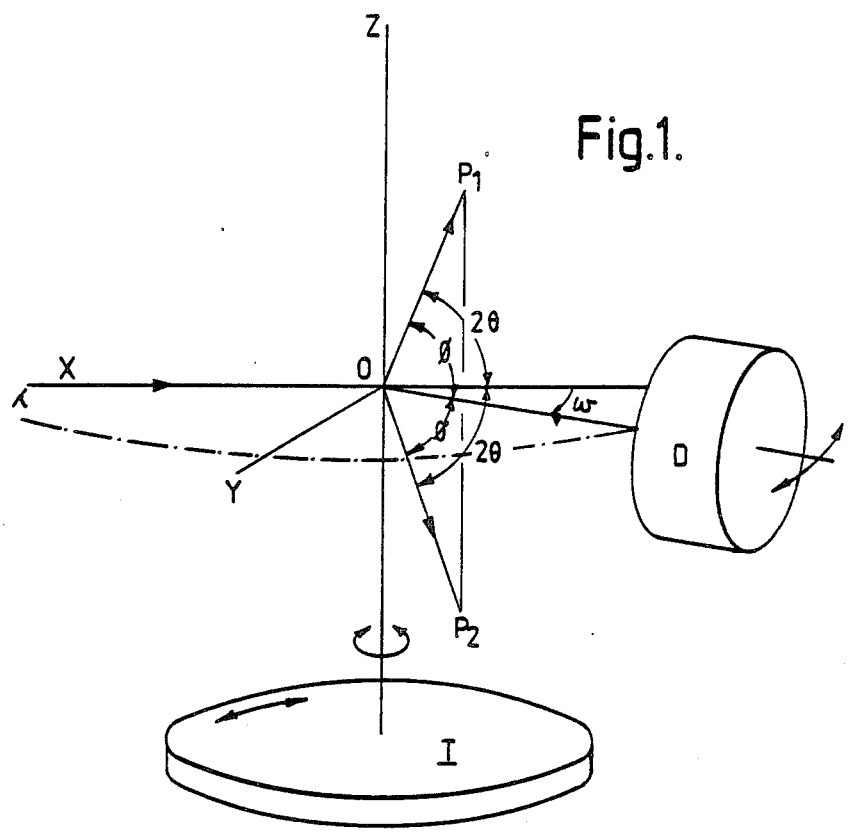
FIG. 1 is a diagram illustrating the method of adjusting the orientation of crystals according to the present invention.

FIG. 1 is a diagram of an X-ray diffractometer in which a single crystal specimen is located at the origin O of the orthogonal axes XYZ, such that a narrow X-ray beam along the axis XO impinges on the specimen and is reflected to a wide aperture detector D whose axis lies in the plane XOY (hereinafter referred to as the equatorial plane). The crystal specimen is mounted on a turntable T to permit rotation about the axis OZ perpendicular to the equatorial plane.

If the Laue symmetry of the specimen contains one or more planes of symmetry, adjustments must be made to the orientation of the crystal to bring one of these planes of symmetry into coincidence with the equatorial plane.

The detector D may comprise an image intensifier system in which the intensity of reflexions impinging on a fluorescent screen is amplified. This may be, for example, by means of a large-aperture image intensifier tube, or a smaller aperture intensifier tube receiving the images via a lens.

The detector is so disposed to pick-up several pairs of reflexions (symmetrical diffracted beams from crystallographically related sets of planes) of which $OP_1$ and $OP_2$ are a typical pair. These reflected beams lie in the same azimuth respectively above and below the equatorial plane XOY and if the crystal is set accurately with one of its plane of symmetry parallel to XOY, the two reflexions $OP_1$ and $OP_2$ are also symmetrical with respect to XOY.

Rotation of the crystal around the axis OZ causes the pairs of reflexions to move in the same direction across the screen of the image intensifier and because Braggs' Law always holds but the Bragg angle $\theta$ is changing, the wavelength of the diffracted beam varies as a function of, the angular displacement, i.e. $\lambda = 2d \sin \theta$, wherein $\theta = f(\omega)$.

At a certain point during the rotation, however, the wavelength chosen will coincide with that of the very intense monochromatic radiation and the relevant reflected intensity suddenly increases. If rotation continues the selected wavelength continues to change so that the intensity dies back to that corresponding to the white radiation profile. The momentary brightening of the diffracted beams as the crystal passes through this position is referred to as a "flash" for that is how it appears on an image intensifier screen. In general, reflexions $OP_1$ and $OP_2$ will not flash at the same angular setting ($\omega$) of the crystal, so that during rotation they do not flash simultaneously. Lack of simultaneity can be checked by oscillating the crystal rotation $\omega$ to and fro through the two flashing positions, and, by noting the order in which they flash, it is possible very quickly to adjust the orientation of the crystal by tilting the crystal on its mounting about an axis parallel to the OY axis or as near as possible thereto, to achieve simultaneity of flashing. After each tilt adjustment the remaining error can be assessed by rocking the crystal through the flashing position. When simultaneity is achieved the crystal is accurately set with a plane of symmetry parallel to XO, the X-ray beam. A mis-setting of only a few hundredths of a degree will produces a distinct lack of simultaneity even to the unaided eye but with instrumental comparisons much smaller errors can be detected. However, simultaneity is hardly affected by even a relatively gross error in the orientation of the crystal around XO. To detect and remove this, at least one other pair of reflexions at a value of $\omega$ well-removed (about 90°) from the first must be made to flash simultaneously. This ensures that the plane of symmetry is accurately parallel to two different directions in the XOY plane and is thus accurately perpendicular to OZ. In such a setting each pair of reflexions encountered as changes will in turn flash simultaneously. If the crystal is translated so that the incident X-ray beam impinges on a different part of the crystal, this procedure offers a quick and very sensitive means of detecting orientational discontinuities within the crystal.

In practice, and for economy, it is preferred to use detection means comprising two smaller-aperture detection devices, one for each of the diffracted beams $OP_1$ and $OP_2$. The required relative position of these two detectors can be predicted for standard materials and pre-set and the crystal rotated about OZ until each detector intercepts a reflexion. A slower sweep (around OZ) can then be made to identify flashes.

Figure 2:
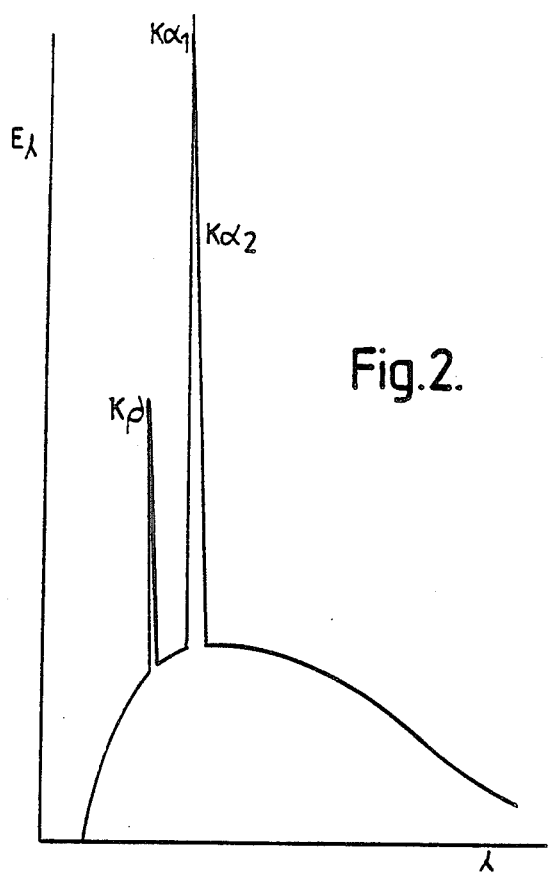
FIG. 2 is a graph showing the output energy profile (as a function of λ: the wavelength) of a typical X-ray diffraction tube operated above the critical voltage of the target element.

Because the test is for simultaneity and not quantitative, it is not necessary to use a stabilised X-ray generator, which is expensive. Also, because the intensity of the characteristic lines is much greater than that of the continuous radiation at other wavelengths, as shown in FIG. 2, there is no need for high-power X-ray tubes or highly sensitive detectors.

The method of this invention is not restricted to crystals having a mirror plane in the Laue symmetry parallel to the equatorial plane. It is equally applicable to any crystal whose reciprocal-lattice points occupy mirror-related positions even when the associated intensities are not equal and, for this reason, the plane which is to be moved into the equatorial plane will be designated the mirror or "m" plane. This looser prerequisite on the crystal and its possible settings makes the invention applicable to virtually all high-symmetry and most low-symmetry materials of current interest.

Of the pairs of reflexions that could be used for flashing, the most suitable are those steeply inclined to the equatorial plane (to ensure high sensitivity to mis-setting), and for convenience having deviations ($2\theta$) from the incident beam lying between about 60° and 120°—in the XOY plane approximately ±45° to the normal to the X-ray beam (FIG. 1). The number of potentially useful pairs, their indices and the magnitudes of their deviations ($2\theta$) can be obtained with the aid of a simulation computer program. They depend on the choice of a characteristic X-ray wavelength appropriate to the lattice dimensions of the specimen, but as stated above, it is preferred to use the whole unfiltered output of the X-ray tube—both continuous and characteristic radiations. (see FIG. 2).

The sensitivity to mis-setting is always greater for an error around OY than for an equal error around OX and the disparity is maximal when the crystal lies in or close to its intended orientation. This fact is exploited to enable rapid convergence of adjustments.

The above described method is applicable at different stages in the production of semiconductor wafers. It can be used to adjust or set the orientation of a single crystal or small specimen, a boule in readiness for mounting, a mounted boule prior to slicing into wafers, or a wafer prior to polishing.

Figure 3:
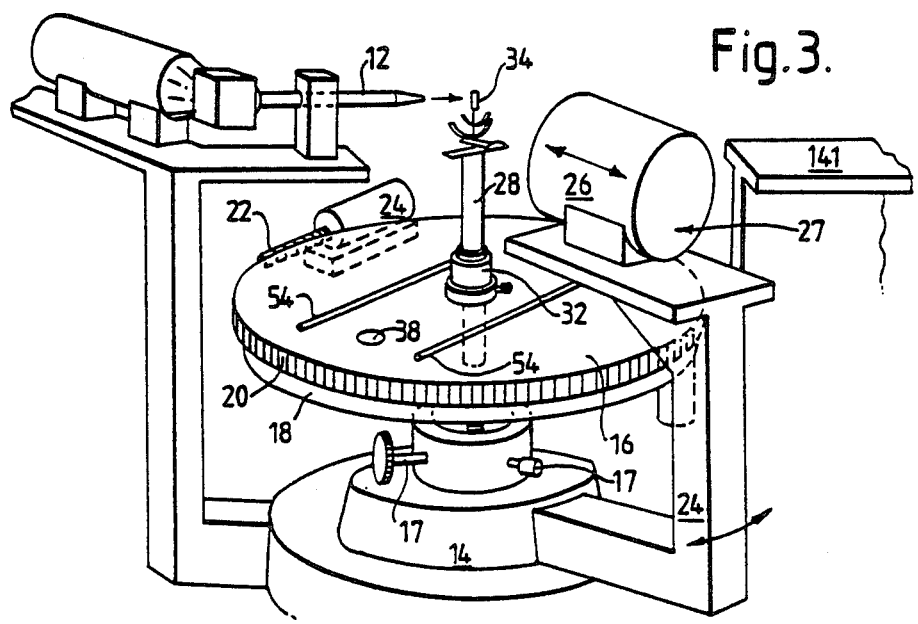
FIG. 3 is a perspective view of apparatus for adjusting the orientation of a crystal by the method of the present invention.

In one embodiment of apparatus shown in FIG. 3 different crystal mountings can be fitted, so enabling the apparatus to be used in all the applications referred to above.

The apparatus comprises an X-ray diffractometer having an X-ray source 10 and a standard single-crystal collimator 12, both attached to the base 14 of the diffractometer and prealigned to produce a narrow X-ray beam (along XO) that intersects and is perpendicular to a vertical axis (OZ), the axis of the diffractometer; the horizontal plane containing the axis (OX) of the X-ray beam is referred to as the equatorial plane of the diffractometer. A circular table 16 on which various crystal holders can be mounted rests on ball bearings that run in a groove (not shown) in the top of a support table 18 which does not rotate but, whose height can be adjusted by a rack and pinion driven by knob 17 and set by a clamp 19 to allow the specimen to be brought into the equatorial plane (XOY) regardless of the size of the crystal specimen or the kind of specimen holder in use. Table 16 is centred by a boss (not shown) that fits into a circular hole in table 18 and has around its rim a worm wheel 20 turned by a worm gear 22 driven by stepping motor 23 mounted on an extension to table. Worm gear 22 is spring loaded against the worm wheel 20 but can be disengaged manually to allow rapid changes of the table's position.

Also mounted upon the base 14 for angular displacement relative thereto about the vertical axis (OZ) is an arm 24 carrying X-ray detecting means in the form of a wide aperture image intensifier 26 having a fluorescent screen 27 for observation by the operator of the diffractometer. Other X-ray detecting means such as scintillation counters may be used as will be described below, and these too can be mounted upon arm 24.

Figure 4:
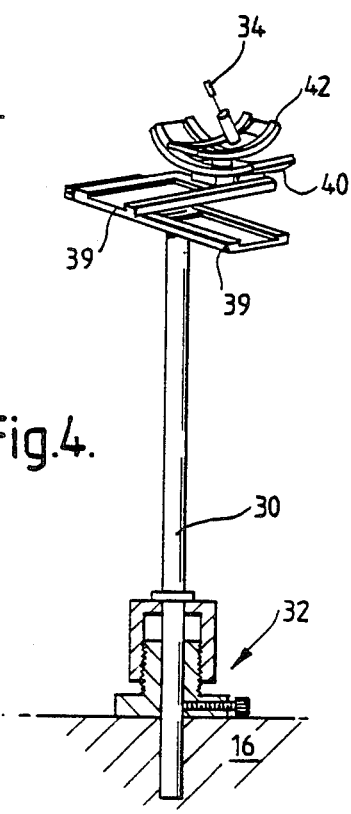
FIG. 4 is a perspective view to an enlarged scale of a goniometer forming part of the apparatus of FIG. 3.

In FIG. 4, the diffractometer is shown fitted with a goniometer 28 mounted upon a spindle 30 passing through a hole in the centre of the table and having thereon an adjusting ring or collar 32 whereby the heigh of the spindle can be set to a desired value. The goniometer head 28 which is shown in more detail in FIG. 4 may be of a conventional kind having the usual four degrees of freedom and enables use of the diffractometer for the purpose of setting a seed or other small crystal specimen 34.

Referring to FIG. 1, an X-ray beam is directed along the axis OX to impinge upon a crystal at the origin O of orthogonal axes XYZ. A detector which may comprise the "m-plane" of which is approximately perpendicular to the axis of the spindle 30. Alternatively, if the "m-plane" of the specimen is approximately parallel to the axis of the spindle 30, the goniometer 28 is mounted horizontally as shown in FIG. 5 by inserting spindle 30 in a bracket 36 located on the table 16 by pins which fit in the central hole in the table and another hole 38 provided for the purpose. The spindle 30 is spring loaded to permit horizontal (centering) adjustment by means of an adjusting ring or collar 32a around the pillar on the reverse side of the bracket 36.

In use of either of the arrangements referred to, the crystal 34 is first centered on the axis of the spindle 30 by means of cross-slides 39 (FIG. 4) on the goniometer head 28. The desired point on the specimen is then brought to the origin O (FIG. 1) in line with the X-ray source by use of the adjusting ring or collar 32,32a or by knob 17 and clamp 19. The X-rays are then switched on and the spindle turned to bring the lower arcuate slide 40 of the goniometer head 28 near to the most sensitive position, i.e. for tilting about OY in the arrangement of FIG. 3. Table 16 is then turned a little in either direction to find a suitable pair of reflexions that flash near the centre of the field of view. Adjustments are made manually to the lower slide 40 to get as close as possible to simultaneous flashing. The table (or spindle—FIG. 5) is then turned by about 90° and is panned a little in either direction to find another flashing pair. The process of alternate adjustment and flashing is repeated but adjustments are made this time on the upper arcuate slide 42. The process is repeated making further minor adjustments alternately to the upper and lower slides 40 and 42 until flashing is simultaneous for all pairs of reflexions. The sequence is rapidly convergent.

If the crystal 34 is the seed for a new boule it can be transferred to the boule-support stem with the aid of a standard single-crystal transfer device such as is well known to one skilled in the art.

The majority of boules are of f.c.c. materials grown elongated along [111] and the wafers are intended to be cut parallel to (111). Such crystals have Laue symmetry m3m with three planes of symmetry parallel to [111]. The methods used hitherto for setting a boule aimed only at getting the two angular corrections needed to set [111] parallel to datum lines on both the diffractometer and cutter. But the method of this invention aims additionally to bring one of the "m-planes" into the equatorial plane, and, although the range of rotational adjustment needed for that is usually 30°, it can be as high as 90°. As a result the boule is preferably set in two stages. In the first stage the rotational error of the boule is reduced to the angle ca. 8°, prior to mounting in the usual way using adhesive. A quick approximation will suffice since the boule is likely to move a little as the adhesive hardens. The mounted boule is then set accurately in the second setting stage.

Figure 7A:
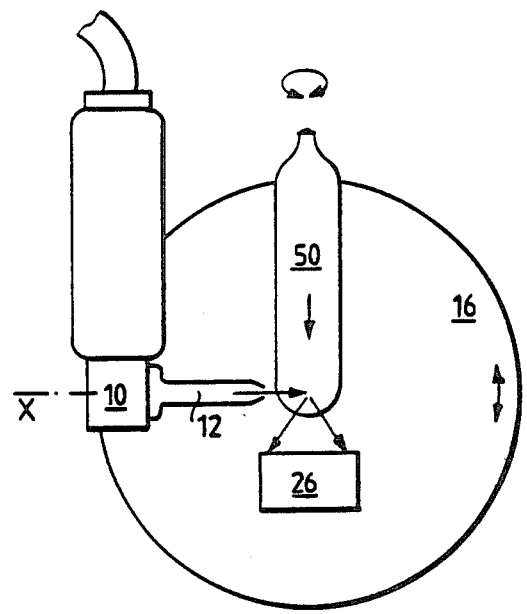
FIGS. 7a and 7b are diagrams illustrating different stages in setting an unmounted boule.

For the setting of an unmounted boule 50 the goniometer head 28 in the embodiments of FIGS. 3 to 5 is replaced by a carriage assembly 52 as shown in FIGS. 6 and 8 which runs on rails end-on broadside 54 fixed to the table 16. The use of the end-on and broadside geometries shown in FIGS. 7a, b and of an image intensifier are preferred for the first stage as the deffraction pattern is then the easiest to interpret and to convert into angular corrections.

The carriage assembly 52 includes a platform 56 above which the boule is supported on three small rubber-tyred wheels 58 two of which are rotatable by means of a stepping motor 60 and shaft 62 in order to rotate the boule. Platform 56 rests upon a jacking module 64 having in its underside V-grooves by which the module 64 is located on and supported by the axles of a bogie 66. Together the bogie 66 and the module 64 afford the same four degrees of freedom as the goniometer head 28 in FIGS. 3 to 5, the carriage being movable longitudinally by running the bogie 66 along the rails 54, and transversely by sliding the module 64 along the axles of the bogie 66. Transverse setting of the module 64 to a desired position is achieved by turning a thumb wheel 68 on a screwed shaft (not shown) rotatably mounted in the bogie and into engagement with which a half nut 72 is biased by spring 74. Tilting about two horizontal axes (parallel to the major and minor axes of plate 56) is achieved by three adjustable jacks 64a to 64c the heads of which protrude through the top of module 64 to engage recesses forming a hole 76a, slot 76c and plane 76b locating system in the underside of platform 56. The structure and operation of the jacks will be described in more detail below. When setting an unmounted boule 50, only jacks 64a,c are used, these being driven antisymmetrically so as to tilt platform 56 about its minor axis and the boule axis in a vertical plane.

Preliminary adjustments are made by hand without X-rays. Thus, table 16 is rotated to bring the boule into the broadside position (FIG. 7a) and its height adjusted by the knob 17 and clamp 19 to bring the boule axis a little below the to bring the boule axis a little below the equatorial plane. Bogie 66 is rolled along rails 54 until the convex end of the boule meets the tip of a distance gauge 78 which marks the origin O (FIG. 9). Gauge 78 is mounted above the collimator 12 and hinged so that it can be retracted to allow detector 26 to be advanced along arm 24 and close to the origin O with its axis along OY.

Figure 7B:
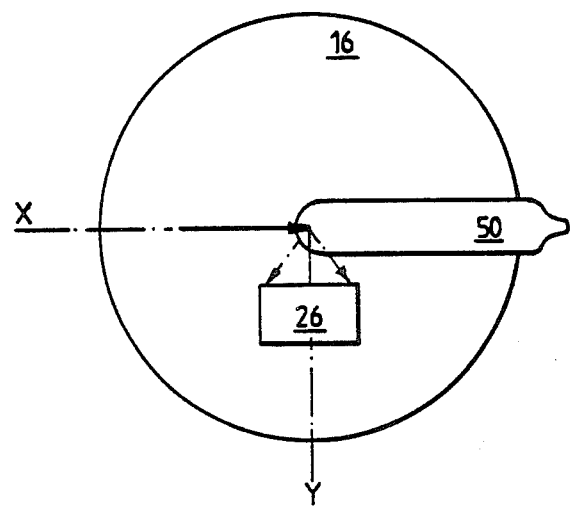

With X-rays on, stepping motor 60 is activated by the operator and the boule 50 thereby rotated until the diffraction pattern, visible on the screen 27 of the image intensifier 16, exhibits rows of spots that are either parallel to or taper symmetrically about an approximately horizontal line through the midpoint of the screen. It is important that the positions at least (and usually the intensities too) of the spot above and below this line approximate to mirror images. Panning table 16 with the supported boule 50 around OZ by means of stepping motor 24 and worm drive 20,22 causes the "symmetrical" pairs of spots in the pattern to move across the screen together, each pair flashing at distinctive positions. A selection is made of a pair that flashes when the boule axis nearly parallel to OY, and the boule is rocked about this position by means of table 16 while small adjustments are made between flashes via stepping motor 60 until the pair flashes as nearly simultaneously as possible. Frequently this approximation will be deemed close enough, in which event no further action is called for. But if further correction is needed, table 16 and the boule 50 are moved to the end-on position (FIG. 7b) and another pair of flashing reflexions is found. Platform 56 is then tilted by means of jacks 64 until the nearest approximation to simultaneity is achieved for this pair. In exceptional circumstances it may be necessary to repeat the processes in the end-on and broadside positions.

The X-ray source is then switched off, the enclosure opened, the boule lifted out and placed on a baseplate covered with adhesive which is then set aside to harden. It may be convenient before lifting it to make lines on the sides of the boule (e.g with a height scriber) to facilitate reproducing the orientation on the baseplate.

In the above described embodiments setting of the orientation of the crystal specimen is performed manually. Automatic operation is, however, possible and is preferred since, in industrial practice, operation of the X-ray diffractometer must be carried out remotely from outside a radiation safety enclosure. The application of the present invention to the next stage in the manufacture of semiconductor wafers—the setting of a mounted boule prior to cutting—is therefore described with reference to a computer controlled embodiment of X-ray diffractometer in accordance with the invention. It will be appreciated by those skilled in the art that the control techniques described may also be applied to other embodiments of apparatus for use at other stages in production.

Figure 10:
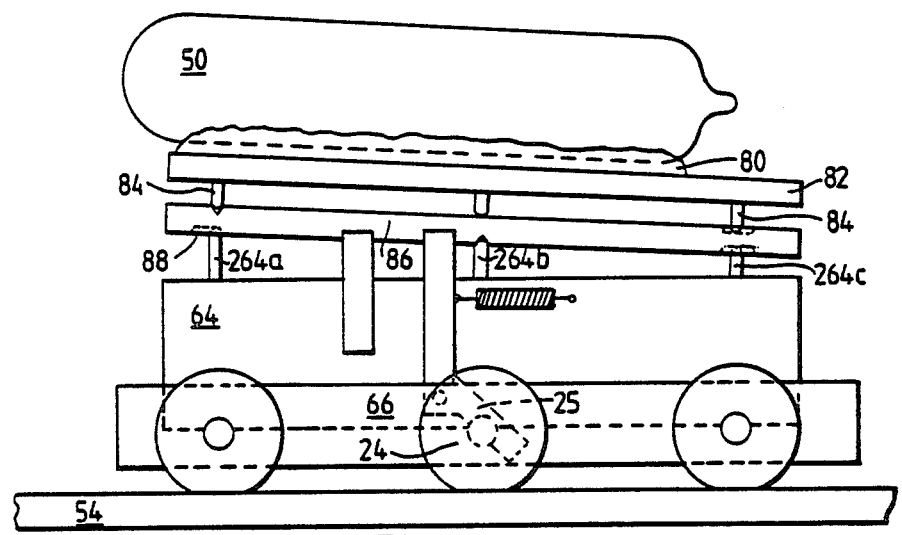
FIG. 10 is a side elevation of a carriage assembly for mounting on the turntable of the apparatus shown in FIG. 3 to enable setting of the orientation of a mounted boule.

After the boule 50 has been mounted on a baseplate 82 as shown in FIG. 10 and the adhesive 80 has set it is required to adjust the boule (and baseplate) precisely on the diffractometer to bring its [111] axis parallel to a datum line. This entails making corrections around all three axes (OX, OY and OZ) and then reducing them to the two corrections needed on the cutter. The relevant correction data may be transferred with each boule to the cutter in either analogue or digital form. In the following, both will be described. The method of deriving the corrections is the same in each case but different base plate designs are necessary.

Figure 11:
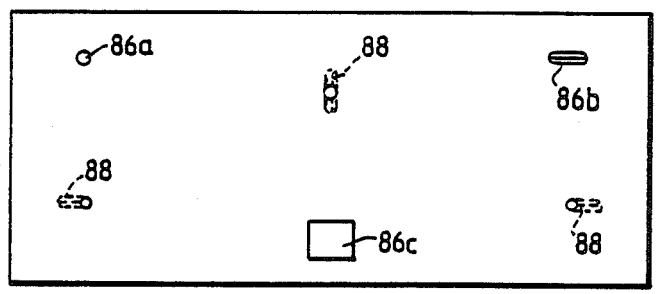
FIG. 11 is a plan view of an interface plate forming part of the carriage assembly shown in FIG. 10.
Figure 12:
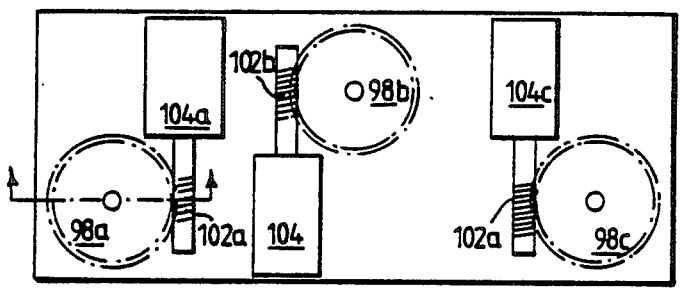
FIG. 12 is a schematic cross-section in plan of a jacking module forming part of the carriage assembly shown in FIGS. 6, 8, and 10.
Figure 13:
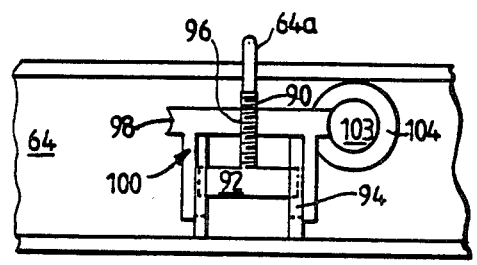
FIG. 13 shows one of the three jacks in the jacking module of FIG. 12.

The boule, already mounted upon a base plate 82 having three domed feet 84, is placed upon an interface plate 86 on which it is located uniquely by a hole 86a, slot 86b, plane 86c system and which in turn is supported by the three jacks 64a–c of the jacking module 64, engaging in V-slots 88 in the underside of the interface plate as shown in FIG. 11.

Each jack 64a, b, c has a threaded stem 90 the 92 of which runs in slots, or is otherwise restrained against rotation, within a hollow cylindrical body 94. The threaded stem 90 is engaged in a threaded hole 96 at the centre of a worm wheel 98 located on the body 94 for rotation relative thereto by a boss or skirt 100 which fits around the body. As the worm 102 engaging the worm wheel 98 is turned in one or other direction by a stepping motor 104, so the jack is raised or lowered.

Table 1 shows the effect of driving some or all of the stepping motors 104a–c simultaneously in the same (+) or opposite (−) directions.

TABLE 1

| a | b | c | Jack |
|---|---|---|---|
| + | + | + | height adjustment |
| + | 0 | − | tilt the boule about its minor axis: this preserves the height of the midpoint between jacks a, c to provide with jack-b a constant pivot line, |
| 0 | + | 0 | half-range rotation around the boule's major axis, |
| − | + | − | full-range rotation around the boule's major axis. |

The following steps for setting the boule can be effected manually or under computer control; Step a: the boule is set in the broadside position, (position A, FIG. 17) and the orientation around the boule axis is adjusted. If the correction needed is small enough it suffices to drive jack 64b only; otherwise double the correction range as shown in Table 1; Step b: The boule is then set in the end-side position (position B, FIG. 17) and the procedure repeated but making antisymmetric adjustments on jacks 64a, c only.

Adjustments with the boule alternately in the end-on and broadside position (steps a and b) are then repeated to convergence which should bring the "m-plane" into coincidence with the equatorial plane. This can be checked by detecting a number of flashing pairs between position A and B and testing their simultaneity too. However, this does not determine the position of the [111] axis in the equatorial plane. For that, table 16 is rotated by an angle $\chi \pm \Delta$, the angle $\chi$ being readily calculable from the known lattice parameters, the indices of the flashing reflexions and the charcteristic wavelength in use. The angle, $\Delta$ if needed, is a deliberate offset.

The boule baseplate 29 assembly is then ready for removal to the cutter.

It may often be impossible to get an image intensifier close enough to intercept the desired pair of reflexions. Instead if visual control is acceptable, a large fluorescent screen can be mounted farther back and its image projected by a lens on to a Vidicon for TV screen display.

For computer control, this Vidicon can or produce output signals representing the intensity of the reflexions with reference to the X-Y coordinates thereof. These are then analysed by the computer.

Figure 14:
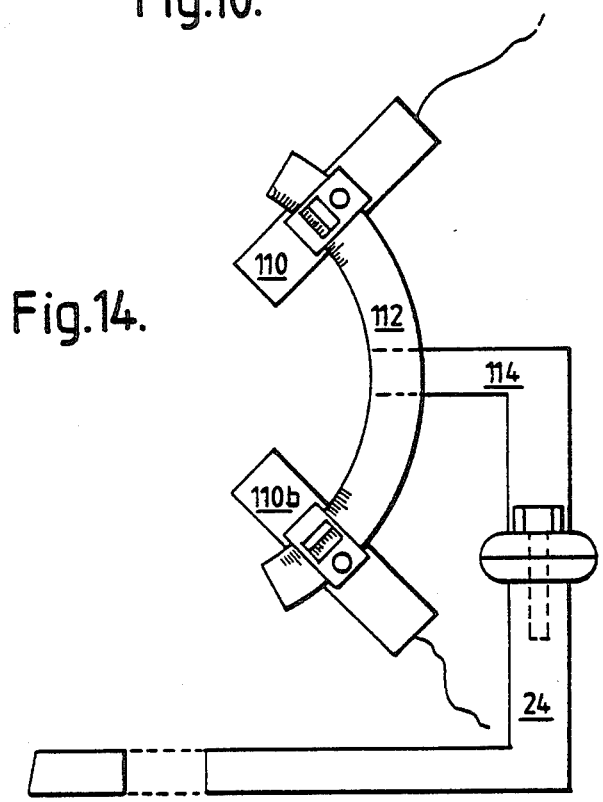
FIG. 14 shows an embodiment of detecting means comprising symmetrically disposed scintillation counters for mounting in the apparatus of FIG. 3.

In another embodiment susceptible of computer control, two smaller aperture detectors 110a and 110b are used as shown in FIG. 14. Each detector can be preset on an arcuate scal 112 to intercept one of the symmetrical reflexions for a correctly set boule. The scale is mounted by a bracket 114 on the arm 24. The two detectors 110a and 110b are standard X-ray scintillation counters with photo-multiplier, each having an aperture of ca. 20 mm placed close to the specimen where it can intercept the desired reflexion even if the boule is misset by ca. 10°. The usual pulse-height analyser should not be used with these detectors and the pulses corresponding to all photons recorded by each detector are fed directly into two computer locations where they accumulate.

Figure 15:
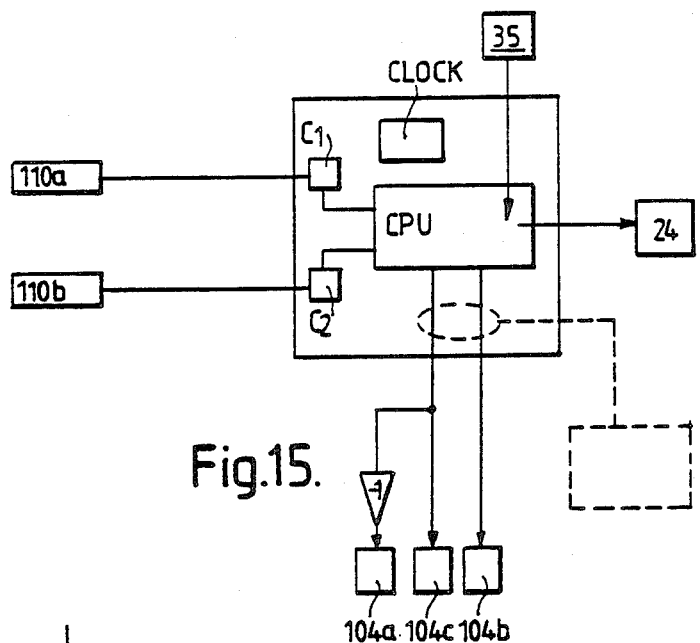
FIG. 15 is a block diagram of an embodiment of computer controlled apparatus for setting the orientation of a single crystal according to the present invention.

FIG. 15 is a block diagram of a computer control system in which the computer has a centrol processor unit CPU and locations designated as counters $C_1$ and $C_2$ to which the output signals of the scintillation counters 110a and 110b are fed. The computer control system per se will not be described in detail since the construction of such a system forms no part of the invention and will in any event be well known to those skilled in the art.

The edge of the diffractometer table carries a digitally-divided scale (not shown) that is read by transducer 35 and the $\omega$ values (FIG. 1) are fed to the computer. At regular increments, say $\Delta\omega = 0.002°$ or $0.005°$, the computer receives an interrupt signal so, though high accuracy of the absolute value of $\omega$ is not so important, a high degree of uniformity of the increments $\leq 0.001°$ is essential.

Figure 16:
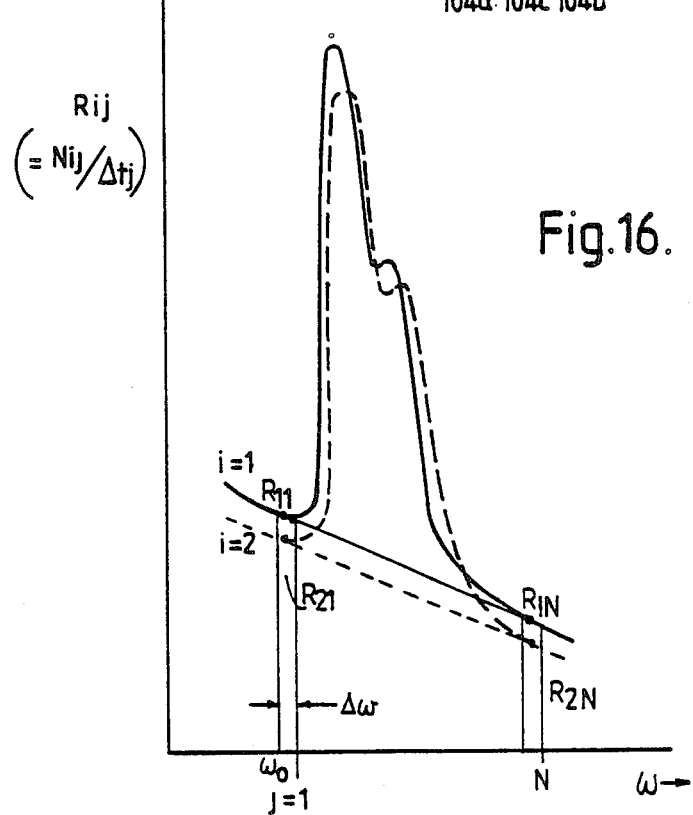
FIG. 16 is a graph illustrating the technique by which the apparatus of FIGS. 14 and 15 is brought automatically to a position wherein simultaneous flashing of a symmetrical pair of Laue reflexions occurs.

FIG. 16 depicts the count rates on traversing a pair of reflexions that are flashing at slightly different values of $\omega$.

The table 16, driven by the motor 24 under control of the computer, is rotated back and forth about the axis OZ through an angular range that is wide enough to embrace both peaks. The lower extremity of scanning range begins at an arbitrary value, $\omega_o$, and the range contains N increments. At each interrupt the central processor unit CPU of the computer notes the photon count ni where i=1 or 2 in counters $C_1$ and $C_2$ respectively the time $\Delta t_j$ (from the computer clock), and j the increment number beyond $\omega_o$. It then clears the counters $C_1$ and $C_2$, resets the clock, and increments j ready for the next $\Delta\omega$ increment in the scan. In accordance with the computer program these data are converted into rates $Rij(nij/\Delta tj)$ which are used to calculate, according to equation 1 below, and accumulate contributions to the weighted average of j. At the end of the scan, a correction is made (based on the average rates of the first an last increments) to remove the background. The centres of gravity of the two peaks are $\omega_o + [<j>_i - 0.5] \cdot \Delta\omega$ where $$<j>_i = \Sigma Wij \cdot j / \Sigma Wij$$

$$Wij = Rij - [Ri \cdot <n-j> + Rin<j-1>]/<n-1> \qquad 1$$

Use of the computer can reveal a lack of simultaneity, $[<j>_1 - <j>_2] \cdot \Delta\omega$, of 0.001° or less, whereas by eye and image intensifier the limit is ca. 0.01° at best.

As stated above corrections are effected by adjusting the jacks 64a to c which are driven under control of the computer by motors 104a to c respectively. For small corrections around the boule axis (step a) only motor 104b is actuated, but since the corrections required in step b involve antisymmetric adjustment of the jacks 64a and c, the pulse command signals to motors 104a and c are of the same number but opposite polarity. Hence, the motors 104a and c may be connected to a common signal, but one 104a, via an inverter as shown in FIG. 15.

In some circumstances, it may be more convenient to feed the pulse from each detector 110a and 110b via a rate meter and A/D converter into the computer, but for slow scans or those controlled by hand and therefore of uneven scan rate the computer should average the output from each ratemeter for each interval. The cutter normally needs only two angular corrections, viz, the corrections around OZ and around the minor axis of baseplate 82. On rare occasions, however, where it is necessary to introduce a deliberate offset in a particular orientation with respect to the crystallographic axis, the third correction (around the major axis of the baseplate) is also needed.

The corrections can be output in printed form (numerals or bar code) or as perforated paper tape or cardas indicated by P in dotted lines in FIG. 15, and the relevant data slip, stuck to the boule, goes with it to the cutter where the digital correction data can be inserted manually or automatically.

The correction around OZ is derived directly from the ω-scale attached to table 16. But the other correction must be derived from the pulses applied to stepping motors 104. These must, therefore, have means for identifying the zero-tilt position, and for checking that each pulse to the motor is obeyed by one step: no more, no less. The former can be achieved by wiring two microswitches in parallel, one to sense an indent in the top of the skirted worm 98, 100 and the second to sense a similar indent in a disc attached to the drive spindle of the motor. These indents are set to open both microswitches at the relevant zero position and thus interrupt a continuous stream of zeriosing pulses.

The latter condition is achieved by a second microswitch or a photo-diode activated by the stepping motor spindle. It emits a brief pulse as the spindle responds to one command pulse. The response pulses are accumulated in a computer register and the command pulses are adjusted to achieve the correct number of response pulses despite missed pulses or overshoots. The correction angle must be calculated from the number of response pulses and the known dimensions between the jack heads.

Figure 17:
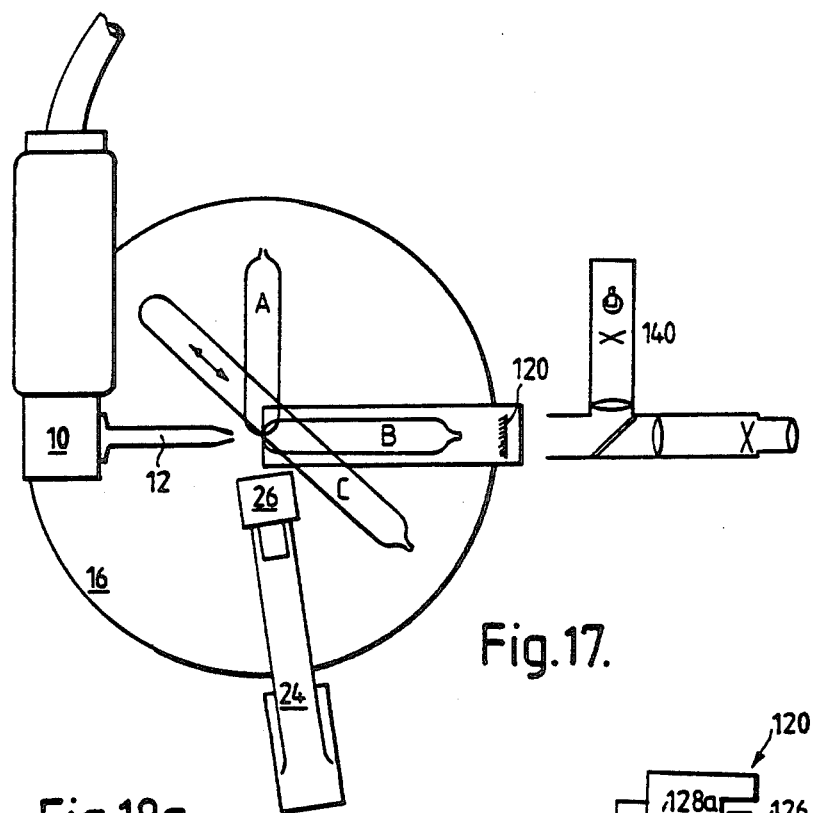
FIG. 17 is a schematic plan view of a modified embodiment of apparatus for setting a mounted boule such that correction data can be transferred with the boule in analogue form.
Figure 18A:
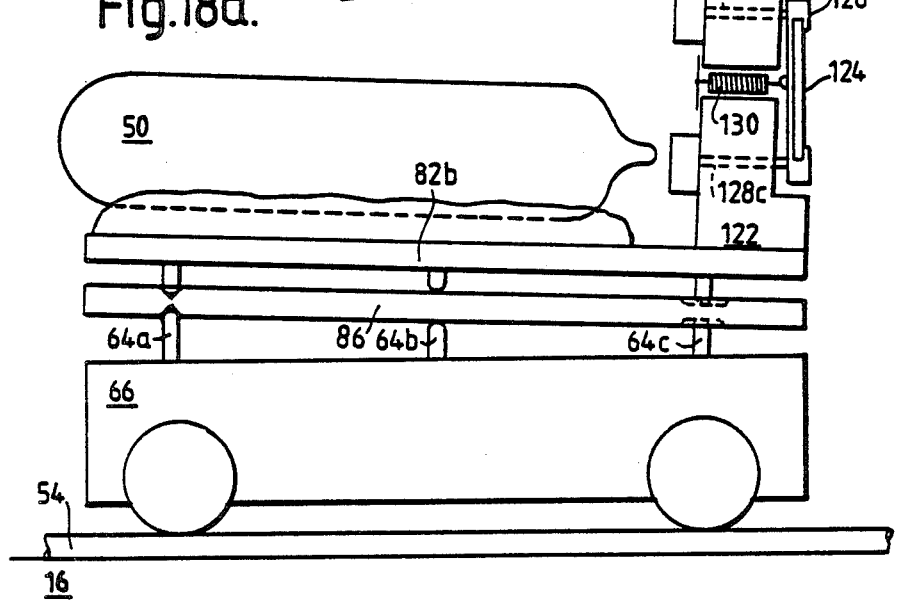
FIGS. 18a, 18b, 18c and 18d show details of a modified base plate forming part of the carriage assembly in the apparatus of FIG. 17.
Figure 18B:
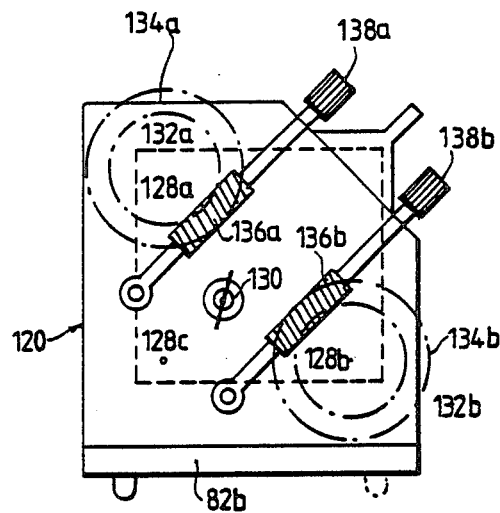
Figure 18C:
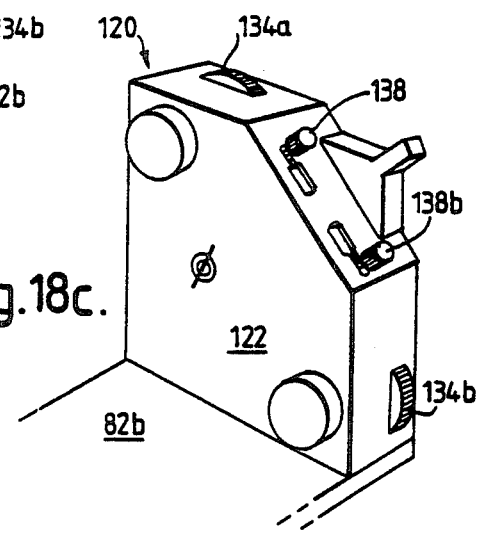
Figure 18D:
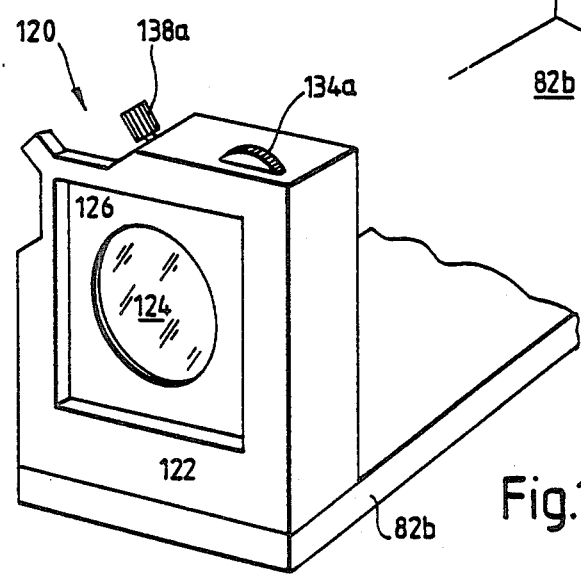

With reference now to FIGS. 17 and 18, for the transfer correction data in analogue form, a baseplate 82b is used to which is attached a mirror assembly 120. After the mounted boule has been set as described above with its [111] axis parallel to a datum line on the diffractometer the mirror is tilted to bring its axis parallel to the same datum line. Then, after transfer to the cutter, corrections are made to the tilt of the cutter bed to bring the mirror normal (and thus the [111] axis of the boule) parallel to the datum line on the cutter before cutting begins. As with transfer of the correction data, in digital form, the correction data is associated with the boule, but this time in analogue form, viz the orientation of the reference axis—the mirror normal. It is to be noted that no angular correction scales are needed on the cutter.

The boule adheres to baseplate 82b on which the mirror assembly 120 is mounted, the mirror assembly comprising a block 122 which carries an optical quality mirror 124 set in a metal mount 126. The mount is held against three studs 128a–c by means of spring 130. Stud 128c is fixed, but the other two are the heads of screws which can be moved manually via the worm wheels 132a, b and thumbwheels 134a, b and the worm gears 136a, b which are disengageable by knobs 138a, b. These allow the mirror to be tilted ca. ±10° about the major and minor axes of baseplate 82b.

An autocollimator 140 shown in FIG. 17 has been mounted upon a support arm 141 (FIG. 3) and prealigned so that its axis coincides with the datum line (OX) of the diffractometer. The user adjusts the tilt of the mirror by means of the knobs 138a, b and thumbwheels 134a, b until the two images seen in the autocollimator coincide. After this, the tilt of the mirror must not be disturbed. The boule baseplate assembly is then transferred to the cutter where a second autocollimator (as collimator 140) is used and angular corrections are made to the cutter bed to get the two images coincident—and the boule therefore ready for cutting. The optical alignments are quick and, with a suitably long focal length in the autocollimators adequate angular precision is available.

To check along the length of a boule for dicontinuities of orientation, the table 16 and with it boule 50 carried thereon, are turned to position C as shown in FIG. 17, and, with the distance gauge 78 (FIG. 9) in position, the boule 50 is moved laterally by means of the disengageable half-nut 72 and the screw until contact is made with the guage. The guage 78 is then retracted and the table 16 rotated as necessary to find a pair of flashing reflexions.

The carriage 52 is then moved along rails 54 while rocking back and forth about OZ through the flashing position. An error around OX or OY will destroy simultaneity; whereas an error around OZ will shift the ω value at which both reflexions flash. In that event, one must then widen the rocking range a few degrees to pick up the flashing pair again. If one is transferring correction data in digital form as described above, it is possible to record the positions of the discontinuities and the values of the correction between each. It is then possible to decide how best to utilize the boule. Because of irregularities in the diameter of the boule the point of impact of the X-ray beam may wander from 0 as the carriage 52 moves along rails 54, and this in turn makes the points of impact of the diffracted beams wander a little across the aperture(s) of the detector(s). With an image producing system such movement can be misleading, but for the computer-controlled system it makes no difference as the profile in FIG. 16 is a function of ω and the output from the 20 mm-wide scintillation counter is independent of the point of impact of the photons.

For setting the orientation of a crystal wafer, a crystal holder such as shown in FIGS. 19a, 19b replaces the platform 56 as shown in FIG. 6. It is designed for handling wafers especially between cutting and polishing. Only one side of a wafer 200 has to be polished and, if the boule has been set for cutting, by the techniques described above, any error between the normal to the cut face and the [111] axis, for example, should be only a fraction of a degree. The corrections or deliberate mis-setting to be applied prior to polishing are therefore small. The crystal holder of FIGS. 19a and 19b is for applying corrections and then transferring the wafer 200 to a spark polisher where no further corrections have to be made before polishing begins. It can readily be adapted to other types of polisher.

The wafer 200 is stuck to an insulating circular boss 202 preferably using dental sticky wax or similar adhesive that will release the wafer on gentle warming, but otherwise holds it firmly. This boss is screwed onto the end of rod 204 which carries a spring 206 that will provide electrical contact to the wafer during polishing. Rod 204 moves easily in a close fitting tube 208 which run down the centre of metal tube 210 which supports the device on both the diffractometer and the polisher. Tube 208 is secured to one end of tube 210 by gimbal 212, and its far end can be moved laterally in the horizontal and vertical directions thereby tilting the wafer, but tube 208 is prevented from rotating about its own axis by the gimbal. Coarse rotational movement of rod 204 within tube 208 is effected manually by means of knurled wheel 214 when worm gear 216 is released from worm wheel 218. Finer rotational movement of the wafer is effected by means of 216,218 after they are re-engaged. The tilting is effected by two face plates 220, 222 which form parts of threaded blocks that move along screws 224,226 mounted inside tube 210. Rod 204 is held firmly against face plates 220,222 by collar 228 and a stiff spring 230 held captive in two telescopic tubes 232a, b. Tube 210 is supported on a platform 56 similar to that shown in FIG. 6, so that it height is adjustable, but instead of resting on three small wheels 58, tube 210 rests on concave blocks 234a, b which have small pegs that engage with indents in the tube to ensure that face plates 220,222 are always vertical and horizonta respectively. Shafts 224, 226 are turned manuall by the insertion of a small key through the wall tube 210.

The circular table 16 is first set in approximately position C (FIG. 17) and bogie 66 moved along rails 54 until the wafer makes conta with distance gauge 78. The platform's position then locked and the distance guage retracted. Th table 16 is turned to bring the crystal holder i position as shown in FIG. 20A and an image intensifier (or fluorescent screen, Vidicon and display) rotated by knurled wheel 24 until an approximate horizontal mirror plane is seen in t diffraction pattern. One pair of reflexions is chosen for flashing and adjustments are made via gear 216 between rocking to get as close to simultaneity as possible. Table 16 is then turned to put tube 210 in approximately position B shown in FIG. 17 and again a pair of reflexions is set in the flashing position. For this setting adjustments have to be made to the height of the movable end of rod 204 via shaft 226 and face plate 222. The adjustments in settings A,B of FIG. 17 are repeated alternately in a rapidly convergent sequence to get two reciprocal-lattice vectors of the "m-plane" zone into the equatorial plane. A final correction has to be applied around axis OZ and this is done as previously described with reference to the setting of a boule, by moving table 16 by $(\chi \pm \Delta)$ where $\chi$ is calculated for the reflexion and $\Delta$ is the deliberate offset. This sets the zone axis parallel to or at a known small angle to the axis of tube 210.

Tube 210 with the attached wafer is transferred to the electro-polisher where the tube is mounted vertically with the wafer as one electrode immersed in oil and suspended a little above the other electrode.

To scan the uniformity of orientation over the area of the wafer it is necessary to move the wafer stepwise, laterally by means of screw 68 and half-nut 72 and at intervals altering the height by means of knob 17, and clamp 19. After each step table 16 is taken through the flashing position and the $\omega$-values of the two flashes are output by the computer. Deviation of the [111] axis in the vertical direction destroys simultaneity, while a deviation around OZ will preserve simultaneiity but shift the $\omega$-value. The horizontal $\Delta\phi_h$ and vertical $\Delta\phi_v$ component of a deviation are calculated from equations $$\Delta\phi_h = \frac{\omega_1 + \omega_2}{2} - \omega_0 \quad (2)$$

$$\Delta\phi_v = \frac{\omega_1 - \omega_2}{2}$$

$\omega_o$ being the value in that part of the boule which had been set to simultaneity.

One further application of the present invention is in monitoring the orientation within a growing boule. In conventional practice discontinuities are rarely discernible until the boule is removed from the furnace and that leads to waste of valuable time and material.

This application is described only in outline and only for the Czochralski method of growing a boule. The boule is supported inside an enclosure which is sometimes pressurised. The lower end of the boule is just below the level of the melt in crucible. As the crystal grows the liquid level falls but can be replenished and the crystal is slowly raised ("pulled") by means of the cooling support stem. This with the boule is slowly rotated to help produce a more uniform cylinder. Since in this application, the boule cannot be rocked, this slow rotation of the boule is exploited to enable monitoring and adjustment to maintain the desired orientation of the growing boule.

FIG. 21 shows schematically apparatus for growing a crystal boule 301 and effecting adjustments during growth to maintain the desired orientation. The crystal is held by a remotely controlled geniometer 302 (similar to that shown in FIG. 4) on the support stem 303 and this is inserted into an enclosure 304 which is sometimes pressurised. The support stem 303 is rotatable and mounted for sliding movement as indicated so that it can lower the seed crystal into a melt 305 contained in cruciple 306.

In the wall of the enclosure 304 at a level above the cruciple 306, is an X-ray transparent window 307 through which an X-ray beam is directed from the X-ray source X to impinge upon the crystal. The equatorial plane is horizontal and the detector D is disposed to receive through another X-ray transparent window (or windows) 308, symmetrical reflexions $P_1$ and $P_2$ which lie in an azimuth normal or near normal to the X-ray beam. The precise location of the windows can be predicted from a knownledge of the crystal material, the crystallographic plane of interest and the wavelength of the charcteristic radiation. Also, the height of the equatorial plane above the level of the melt should be made as small as possible in order that any deviation is detected and corrected with minimum Time lag.

Unless drastic deviations occur it will often be sufficient simply to correct the error and continue growing the boule. Alternatively, to produce a boule without any deviations in orientation, the boule can be reversed into the melt up to the point at which a deviation occurs. The flawed part of the boule is then melted before pulling is resumed. In other cases it might be decided to abort the run to save time and materials.

Immediately prior to inserting the seed crystal into the melt, it may be advantageous to check or adjust its orientation. This is done by pausing at the equatorial plane and rotating the stem 303 to check for simutaneity of flasing reflexions.

During rotation, whether when growing the boule or checking the seed crystal, successive pairs of reflexions will move across the detector D and crystallographic (or Laue) equivalents of a given pair will Traverse the detector once for every 120° of the crystal's rotation, flashing each time. The "m-plane" brought into parallelism with the equatorial plane is in this case the (111) plane. It is not true mirror plane of the m3m Laue symmetry but this does not prevent simultaneity of flashing.

When the seed is initially perfectly set any and every pair of detected reflexions will flash simultaneously as the boule turns. After a deviation, however, different degrees of discrepancy will be detected for each 120° traverse of a particular pair. Under computer control as described above, the computer readily evaluates from the discrepancies, the corrections to be applied to the upper and lower arcs of the remotely controlled goniometer, which are mutually perpendicular and arbitrarily oriented with respect to the three observed pairs.

What is claimed is:

1. A method of determining the orientation of one crystallographic axis in a plane of symmetry of a single crystal, having at least one plane of symmetry, relative to a predetermined set of orthogonal axes comprising:
   directing onto the crystal, along one of said orthogonal axes, an X-ray beam comprising a peak of energy at a given wavelength,
   detecting reflected X-ray energy by means of a two dimensional detector, and
   adjusting the orientation of the crystal while relatively moving the crystal and the beam about an axis perpendicular to an equatorial plane containing the X-ray beam until any pair of reflexions that are symmetrical with respect to the equatorial plane occur simultaneously at the said wavelength of X-ray radiation.

2. A method according to claim 1 wherein the X-ray beam contains white radiation and an intense peak of energy at the said wavelength and comprising detecting a pair or symmetrical reflexions, relatively moving the crystal and the beam about the said perpendicular axis to detect when each of the reflexions flash, adjusting the orientation of the crystal while relatively moving the crystal and the beam about the said perpendicular axis through the two flashing positions until the reflexions flash simultaneously.

3. A method according to claim 1 or claim 2 wherein the orientation of the crystal is adjusted about an axis lying in or parallel to the equatorial plane and transverse, preferably near normal, to the X-ray beam.

4. A method according to claim 3 comprising detecting reflexions that flash at an azimuth as near normal as possible to the X-ray beam.

5. A method according to claim 4 wherein the crystal and the beam are rocked back and forth about the said perpendicular axis between the two flashing positions, adjustment of the crystal being made as necessary until the reflexions flash simultaneously.

6. A method according to claim 4 wherein the crystal is a growing boule, rotating continously relative to the melt, about the axis perpendicular to the equatorial plane, and wherein pairs of symmetrical reflexions are detected continuously or at intervals as the boule is pulled from the melt.

7. A method of determining the orientation of one crystallographic axis in a plane of symmetry of a single crystal, having at least one plane of symmetry, relative to a predetermined set of orthogonal axes comprising:
   directing onto the crystal, along one of said orthogonal axes, an X-ray beam comprising a peak of energy at a given wavelength,
   detecting reflected X-ray energy that flash at an azimuth as near normal as possible to the X-ray beam, by means of a two dimensional detector,
   adjusting the orientation of the crystal about an axis lying in or parallel to the equatorial plane and transverse, preferably near normal, to the X-ray beam, while relatively moving the crystal and the beam about an axis perpendicular to an equatorial plane containing the X-ray beam until any pair of reflexions that are symmetrical with respect to the equatorial plane occur simultaneously at the said wavelength of X-ray radiation,
   adjusting the orientation of the crystal so as to minimize the lack of synchronism between the flashes of a first pair of symmetrical reflexions,
   displacing the crystal through an angle of 90° about the said perpendicular axis and rocking the crystal to and fro about that position while adjusting the orientation of the crystal so as to minimize the lack of synchronism between the flashes of a second pair of symmetrical reflexions and
   repeating the adjustments in each of the above positions alternatively until the reflexions in each pair flash simultaneously.

* * * * *